United States Patent
Grodzins et al.

(10) Patent No.: US 6,621,888 B2
(45) Date of Patent: Sep. 16, 2003

(54) X-RAY INSPECTION BY COHERENT-SCATTERING FROM VARIABLY DISPOSED SCATTERERS IDENTIFIED AS SUSPECT OBJECTS

(75) Inventors: Lee Grodzins, Lexington, MA (US); William Adams, Powell, OH (US); Peter Rothschild, Newton, MA (US)

(73) Assignee: American Science and Engineering, Inc., Billerica, MA (US)

( * ) Notice: Subject to any disclaimer, the term of this patent is extended or adjusted under 35 U.S.C. 154(b) by 0 days.

(21) Appl. No.: 10/190,903

(22) Filed: Jul. 8, 2002

(65) Prior Publication Data

US 2003/0016783 A1 Jan. 23, 2003

Related U.S. Application Data

(63) Continuation-in-part of application No. 09/637,755, filed on Aug. 11, 2000, now Pat. No. 6,442,233, which is a continuation-in-part of application No. 09/325,600, filed on Jun. 3, 1999, now abandoned.
(60) Provisional application No. 60/089,697, filed on Jun. 18, 1998.

(51) Int. Cl.⁷ .............................................. G01N 23/04
(52) U.S. Cl. .......................... 378/57; 378/88; 378/90
(58) Field of Search ............................... 378/57, 82, 86, 378/87, 88, 89, 90

(56) References Cited

U.S. PATENT DOCUMENTS

| | | | |
|---|---|---|---|
| 4,260,885 A | 4/1981 | Albert | 250/277 R |
| 5,007,072 A | 4/1991 | Jenkins et al. | 378/88 |
| 5,491,738 A | 2/1996 | Blake et al. | 378/71 |
| 5,493,596 A | 2/1996 | Annis | 378/57 |
| 5,600,303 A | 2/1997 | Husseiny et al. | 340/568 |
| 5,600,700 A | 2/1997 | Krug et al. | 378/57 |
| 5,642,393 A | 6/1997 | Krug et al. | 378/57 |
| 5,682,412 A | 10/1997 | Skillicorn et al. | 378/98.6 |
| 5,696,806 A | 12/1997 | Grodzins et al. | 378/86 |
| 5,764,683 A | 6/1998 | Swift et al. | 378/57 |
| 5,787,145 A | 7/1998 | Geus | 378/71 |
| 5,930,326 A | 7/1999 | Rothschild et al. | 378/57 |
| 6,118,850 A | 9/2000 | Mayo et al. | 378/83 |
| 6,151,381 A * | 11/2000 | Grodzins et al. | 378/90 |
| 6,192,101 B1 | 2/2001 | Grodzins | 378/55 |
| 6,442,233 B1 * | 8/2002 | Grodzins et al. | 378/57 |

FOREIGN PATENT DOCUMENTS

EP 0 354 045 A2 7/1990 .......... G01N/23/20

* cited by examiner

Primary Examiner—Drew A. Dunn
Assistant Examiner—Allen C. Ho
(74) Attorney, Agent, or Firm—Bromberg & Sunstein LLP

(57) ABSTRACT

A system and method for inspecting an enclosure with penetrating radiation. Radiation side-scattered from an object within the enclosure is detected, allowing the object to be located. If the object is deemed suspect, a volume element of the suspect object is further irradiated with penetrating radiation, and radiation coherently-scattered by the volume element is detected. The energy spectrum and angular distribution of the coherently-scattered radiation are used to characterize the volume element of the suspect object.

27 Claims, 6 Drawing Sheets

X-RAY INSPECTION BY COHERENT-SCATTERING FROM VARIABLY DISPOSED SCATTERERS IDENTIFIED AS SUSPECT OBJECTS

This application is a continuation-in-part of copending application Ser. No. 09/637,755 filed Aug. 11, 2000 now U.S. Pat. No. 6,442,233. Application Ser. No. 09/637,755 is a continuation-in-part of application Ser. No. 09/325,600, filed Jun. 3, 1999 and subsequently abandoned, and claims priority from U.S. Provisional Application No. 60/089,697, filed Jun. 18, 1998. Each of these applications is incorporated herein by reference.

TECHNICAL FIELD

The present invention relates to an x-ray system and method for identifying material within an obscuring enclosure, and more particularly to a system and method using a combination of side-scattered and coherently-scattered penetrating radiation for discriminating target materials.

BACKGROUND ART

The angular distribution of x-ray radiation scattered from a material when the radiation incident on the material is substantially monochromatic provides a well-established method for identifying the scattering material. The basis of the identifying characteristics of the scattered radiation is coherent x-ray scattering from the crystal planes of the bulk material. The well-known Bragg equation governs this so-called wavelength dispersive spectroscopy:

$$\sin \theta = n\lambda/(2d) \quad (1)$$

where d is the spacing between crystal planes, $\theta$ is the scattering angle, n is the order of scattering and $\lambda$ is the wave length of the radiation. Practitioners typically use low energy x-rays for these measurements, for example, the 8 keV (1.5 Å) x-rays from copper produce strong Bragg peaks at large, easily measured, scattering angles.

However, the identification of material in the interior of large containers typically employs radiation of higher energy. In particular, for luggage brought on board aircraft, typical x-ray energies are at least 75 keV, corresponding to a wavelength of ⅙th of an Angstrom. At this energy, the first Bragg peak (the closest to $\theta=0°$) will then be at a very small angle, typically in the range of a few degrees, making wavelength dispersive spectroscopy extremely difficult.

A more practical approach for the use of coherent-scattering at higher energies, suggested by G. Harding and J. Kosanetzky, "Scattered X-Ray Beam Non-Destructive Testing," in Nuclear Instruments and Methods (1989), is to use energy dispersive spectroscopy. In energy dispersive spectroscopy, a polychromatic beam of high energy x-rays is sent through the container and the energy distribution at a fixed scattering angle of a few degrees is used to identify the object. The governing equation is the same as Eqn. 1, written to emphasize the energy dependence:

$$E=\{6.2\}/\{d \sin \theta\} \approx \{6.2\}/\{d\theta\}, \quad (2)$$

where d is the crystalline spacing in Angstroms, $\theta$ is the scattering angle in radians, and E is the x-ray energy in keV. Thus, for example, an x-ray of 100 keV will be Bragg scattered through an angle of about 2° by a crystalline substance with spacings of about 2 Å.

Bragg-scattering inspection systems under current development seek to examine the entire volume of every piece of luggage that enters an aircraft. The hardware to carry out this daunting task is complex and expensive, and is at least 2 orders of magnitude too slow to be effective as a screener at an airport terminal.

Additionally, since the Bragg scattering angles are so low (typically 2°–3°), the collimation requirements on the detector are stringent if a particular volume along the x-ray path into the interrogated volume is to be discriminated. The strict requirement on the collimation of the coherent-scatter detector can be quantified by noting that an uncertainty in the angle results in an uncertainty in the measured energy. Differentiating Equation (2) gives the necessary relation:

$$\Delta E/E \approx \Delta\theta/\theta. \quad (3)$$

To obtain a full-width energy resolution of $\Delta E/E=5\%$, the angular uncertainty $\Delta\theta/\theta$ must be kept to 5%. (A 5% uncertainty is typical of the maximum uncertainty that can be tolerated if the coherent-scatter method is to effectively discriminate between different types of materials.) The collimation must therefore be good enough to limit the acceptance angle to 2° with an accuracy of 5%, a difficult requirement.

The small scattering angles with their tight uncertainty requirements severely restrict the length along the beam that can be inspected by a single coherent-scatter detector, typically to no more than 3 cm. If the position along the beam path of a suspect volume of an inspected enclosure is unknown, then it becomes necessary to make 5 to 10 separate measurements (or, alternatively, to provide the same number of carefully collimated detector elements) to inspect all the voxels (i.e., volume elements) along a given beam path. In one case, inspection times are increased, and in the other, the cost of the system is impacted substantially.

SUMMARY OF THE INVENTION

In a first embodiment of the invention there is provided a method for inspecting an enclosure. In accordance with the method, an enclosure is irradiated with penetrating radiation, radiation side-scattered from an object within the enclosure is detected, and the object is located. On the basis of the side-scattered radiation, a decision is made as to whether the object is suspect. If the object is deemed suspect, a volume element of the suspect object is further irradiated with penetrating radiation. Radiation coherently-scattered by the volume element is detected. The energy spectrum and angular distribution of the coherently-scattered radiation then are used to characterize the volume element of the suspect object.

In accordance with another embodiment of the invention, determination of whether an object is suspect is determined on the basis of the mass density of the object. The mass density is derived from side-scattering, including Compton scattering, where the enclosure is scanned with an x-ray beam generated by a wheel with a plurality of hollow spokes and an x-ray source at its center.

In accordance with a further embodiment of the invention, an object is identified on the basis of mass densities of contiguous volume elements of the suspect object. A volume element of the suspect object is irradiated by aligning a single pencil-beam collimator with an x-ray source and with the volume element of the suspect object.

In accordance with still further embodiment of the invention, the enclosure containing the object is transported on a conveyor belt through an irradiating beam. The radiation side-scattered by the object is subsequently detected. The conveyor belt may then be halted and a volume element of the suspect object irradiated. Coherently-scattered radiation is subsequently detected. As the conveyor belt is halted, detection of objects continues. Alternatively, coherently scattered radiation may be detected without halting the conveyor belt.

In accordance with still another embodiment of the invention, irradiation of an enclosure and irradiation of a volume element of a suspect object are performed with the same source of radiation. The source of radiation moves in the conveyor direction from its location during irradiation of the enclosure to its location during irradiation of a suspect object.

BRIEF DESCRIPTION OF THE DRAWINGS

The foregoing features of the invention will be more readily understood by reference to the following detailed description, taken with reference to the accompanying drawings, in which.

DETAILED DESCRIPTION OF SPECIFIC EMBODIMENTS

Definitions. As used in this description and the accompanying claims, Bragg-scattering refers to coherent-scattering by a lattice and is used interchangeably with "coherent-scattering".

Figure 1:
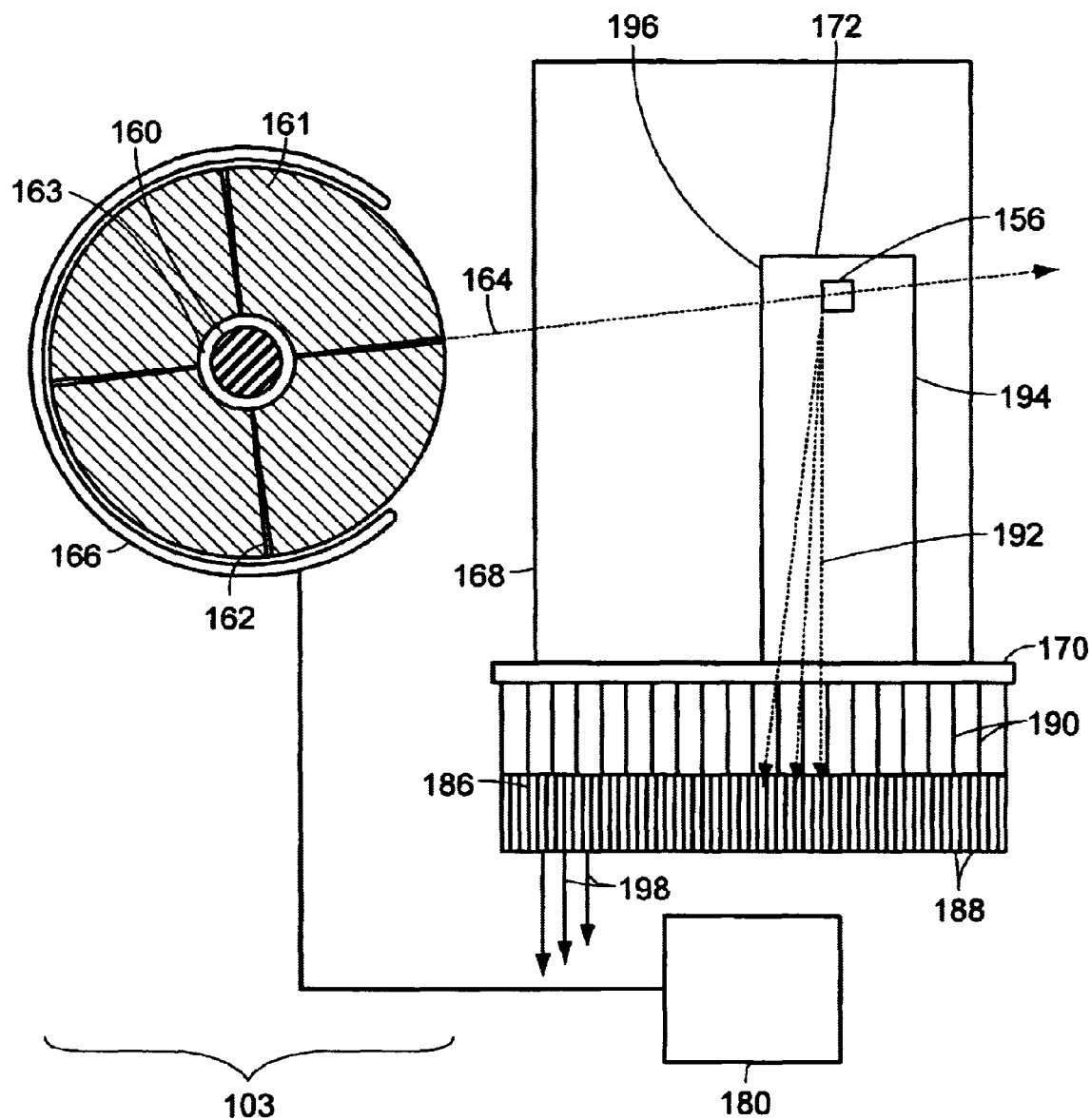
FIG. 1 is a schematic elevation view of a method for x-ray inspection in accordance with embodiments of the present invention using side-scattering.
Figure 2:
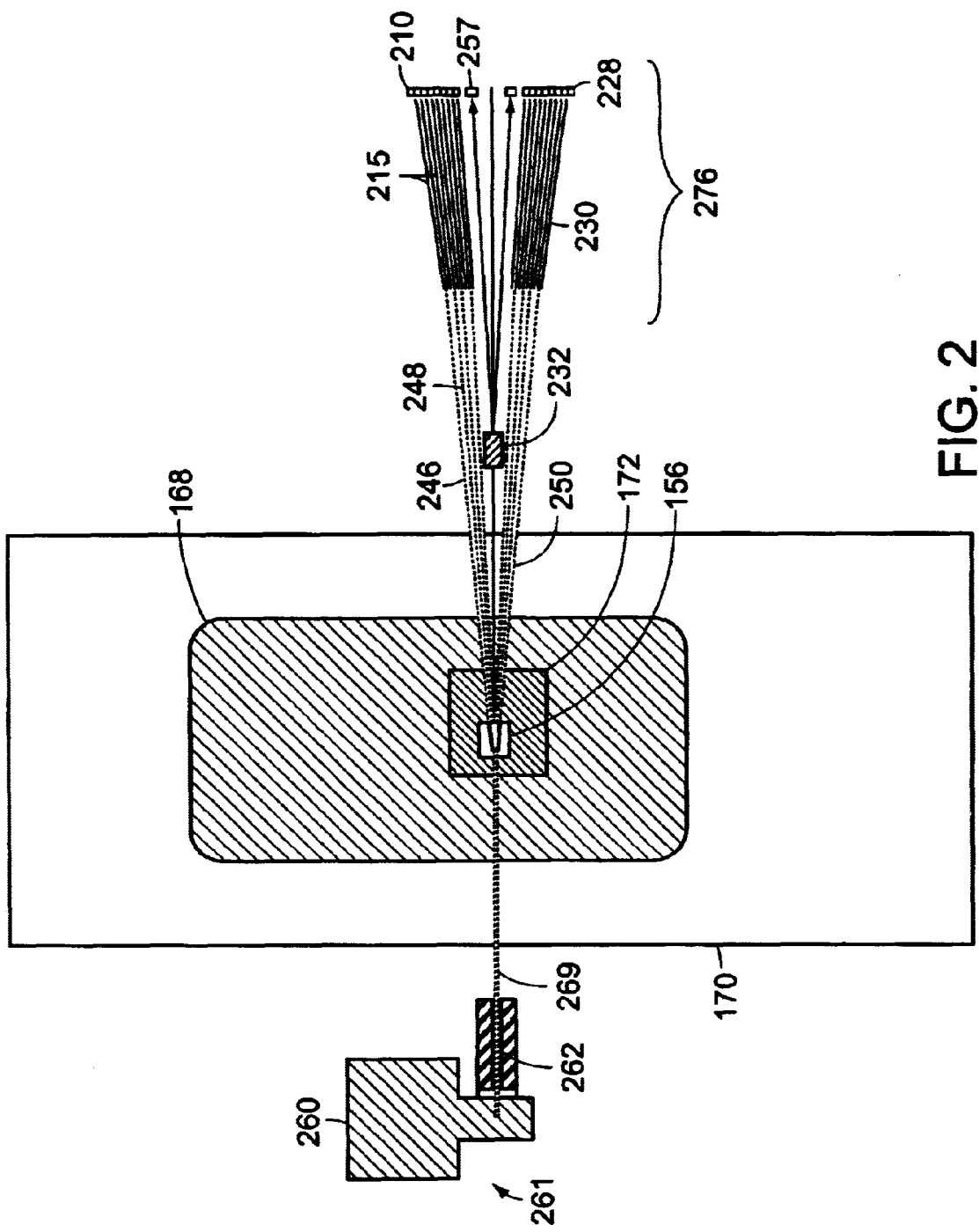
FIG. 2 is a schematic plan view of a method of x-ray inspection in accordance with an embodiment of the present invention using coherent-scattering.
Figure 3A:
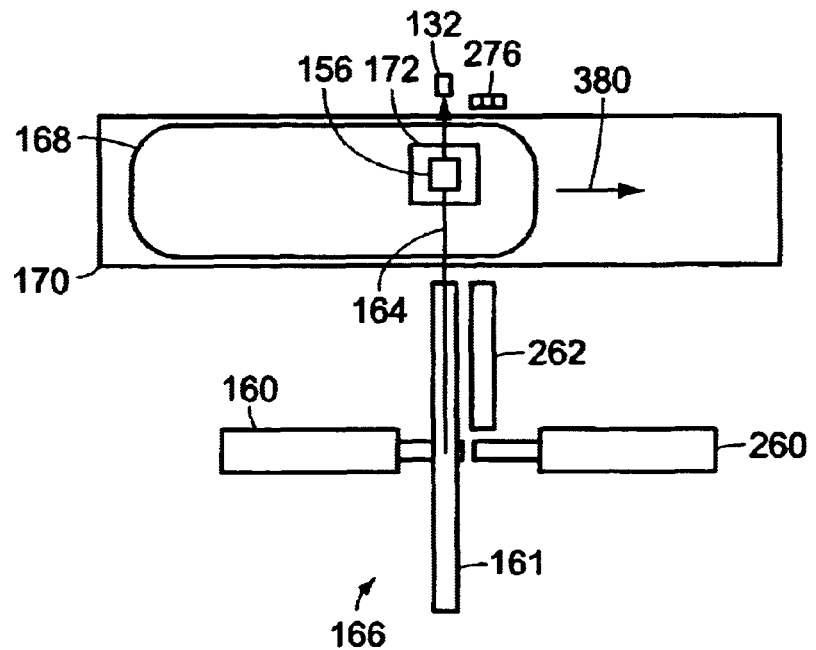
FIGS. 3a–3d depict successive steps of x-ray inspection in accordance with an embodiment of the present invention.
Figure 3B:
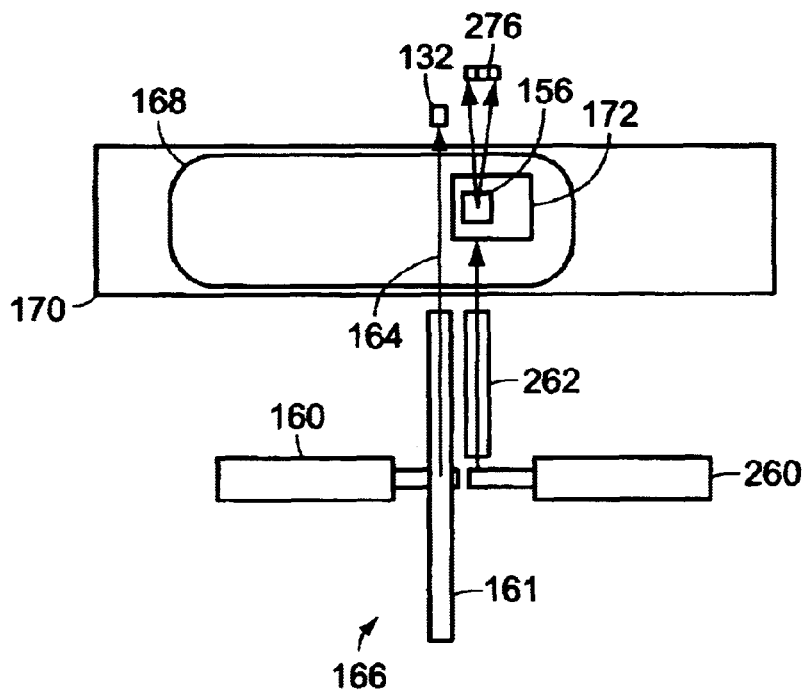
Figure 3C:
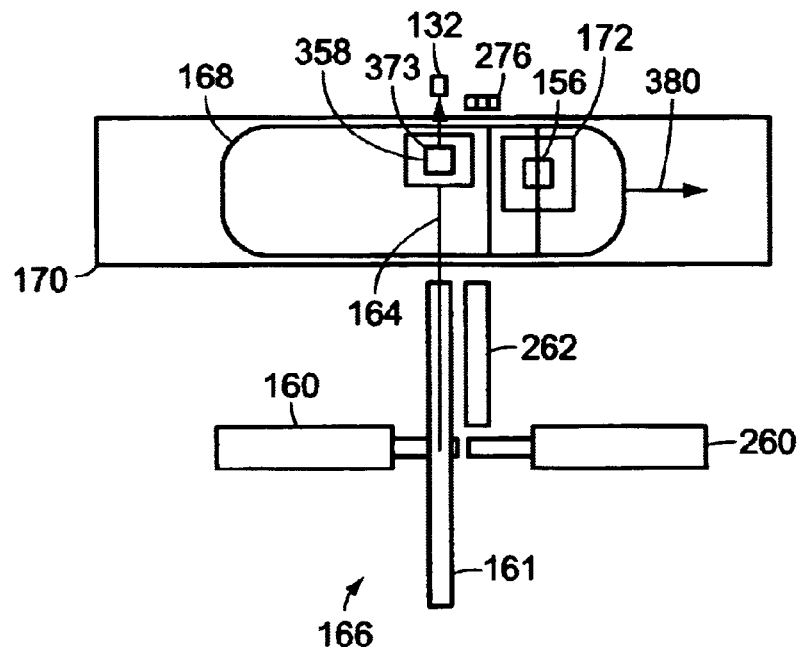
Figure 3D:
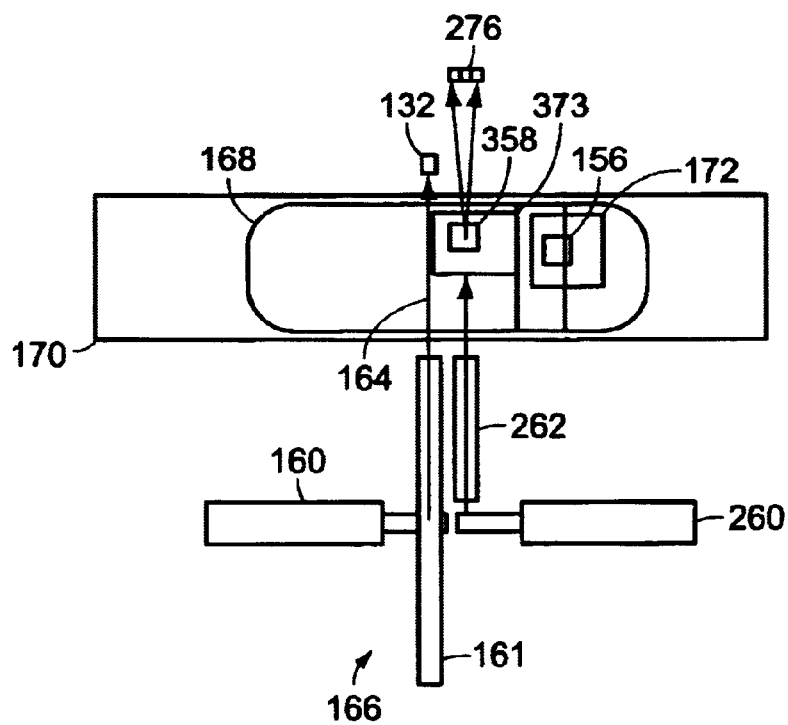

FIGS. 1 and 2 show schematic depictions of the side-scattering and coherent-scattering aspects of x-ray inspection in accordance with embodiments of the present invention. FIG. 3 shows a plan view depicting integration of side-scattering and coherent-scattering for x-ray inspection. FIG. 4 shows schematic depictions of the coherent-scattering aspects of x-ray inspection in accordance with further embodiments of the present invention.

Referring to FIG. 1, an elevation view is shown of a side-scattering x-ray inspection stage in accordance with an embodiment of the invention. Various scanning systems 103 are known to persons skilled in the art to provide for scanning of beam 164 across a region of space which may include a target container (or enclosure) 168 the contents of which are to be scrutinized. In the embodiment of FIG. 1, a source of penetrating radiation generates a beam scanned across enclosure 168. The source may include an x-ray tube 160, for example, and a scanner such as mechanical scanner 166, which includes a rotating wheel 161 of material substantially opaque to x-rays but for hollow spokes 162. Alternatively, electronic scanning of the x-ray beam may be employed. X-ray beams 164 sweep in the plane of the drawing over enclosure 168, Side-scattered x-ray 192 intensities are obtained by side-scatter detector 186 as enclosure 168 is conveyed through the rastered x-rays 164 by the conveyor 170.

Beam 164 has a prescribed cross sectional profile, typically that of a flying spot or pencil beam. Beam 164 will be referred to in the present description, without limitation, as an x-ray beam, and also, without limitation, as a pencil beam. In a preferred embodiment of the invention, a scanned pencil beam, whose position and cross section is well known at every point in time, is used. The cross section of the pencil beam defines the spatial resolution of the images. Typical pencil beam sizes are a few mm in diameter at a distance of a meter from the beam-defining collimation; that is, an angular spread in the beam of <5 milliradians.

Enclosure 168 is scanned by penetrating beam 164 as it is conveyed on conveyor 170. In order to scrutinize subsequently the material comprising an object 172 within enclosure 168 on the basis of the Bragg scatter, it is desirable to resolve the ambiguity as to where along the path of penetrating beam 164 the scatter arises. In that way, the field of view of a subsequent Bragg scatter detector array can coincide with the source of the scatter and the Bragg array can collect the scatter over a range of angles, corresponding to a range of beam energies.

In accordance with various embodiments of the invention, one or more arrays 186 of side-scatter detectors 188 are used for locating the position of object 172 along the x-ray path 164. Techniques for employing side-scatter detectors to determine edges and material characteristics of an object are described, for example, in Grodzins et al. (U.S. Pat. No. 5,696,806, issued Dec. 9, 1997) and Rothschild et al. (U.S. Pat. No. 5,930,326, issued Jul. 27, 1999), both of which patents are incorporated herein by reference.

As shown in FIG. 1, collimators 190 limit the field-of-view of each segment 188 of segmented side-scatter detector array 186 such that, given the direction of beam 164, a volume element 156 within object 172 giving rise to detected side-scattering, including Compton scattering, 192 may be identified. In accordance with the teachings of the patents incorporated by reference, the leading and trailing edges 194 and 196 of object 172 in the slice subtended by beam 164 may be identified. Thus, the extent of object 172 may be determined and the field of view of a subsequent Bragg scatter detector may coincide with a volume element of the object. As taught in Rothschild et al., fiber optic links 198 may be provided to convey scintillation light to photomultipliers (not shown).

It should be emphasized that the side-scatter techniques described herein may provide two independent advances over transmission scanning for identifying suspect objects for scrutiny by coherent-scattering. First, the sides-scatter technique may produce a measure of the mass density of objects. The addition of a mass density information may further restrict the range of possible object material and may thus advantageously result in fewer false alarms, requiring fewer objects to undergo follow-up inspection by coherent-scattering. Second, side-scatter techniques may pinpoint a specific volume element of the object along the beam path so that coherent-scattering may be carried out with a single energy-dispersive detector rather than multiple detectors covering the path of the beam through the enclosure.

Referring to the plan view of FIG. 2, a Bragg scatter detector array 228, displaced from the x-ray beam 269, detects the coherently-scattered radiation if the side-scatter x-ray inspection, as heretofore described, detects that object 172 of enclosure 168 might contain contraband material or other material warranting classification as suspect and more detailed scrutiny. Specific locations of suspect objects are entered into computer 180 that controls the digitally driven components: conveyor 170, position of x-ray source 260, position of collimator 262, and the position of the Bragg array 276. Each component is placed in precise registration for Bragg scatter inspection. Conveyor belt 170 is stopped in front of a collimated source of coherent-scattering x-rays 261 in such a way that the x-ray beam 269 subject to coherent-scattering passes through the suspect object 172.

The Bragg scatter detector array 228 consists of a linear or areal array of energy dispersive detectors 210 such as CdZnTe. Each detector is oriented to share a common field of view with the other detectors and is collimated by a collimator 215 so that the detector is sensitive only to x-rays scattered through a specific narrow range of angles. The Bragg scatter detector array 228 is aligned with the collimated source of coherent-scattering x-rays 261 and with the suspect concealed volume 172 in such a way that the midpoint or axis of the Bragg scatter detector array 228 and collimator array 230 (together, Bragg array 276) aligns with the collimated x-ray beam 269 and the fields of view of the collimators 215 and Bragg scatter detectors 210 coincide with the volume element of the suspect object 156. The suspect objects 172 are examined automatically in sequence.

Because the field of view of Bragg scatter detector array 228 is specifically aligned with a given volume element 156 of a given suspect object 172, each detector 210 of Bragg scatter detector array 228 is sensitive just to radiation scattered from volume element 156 within a narrow range of angles, regardless of the location of suspect object 172 or of volume element 156 within enclosure 168. Thus, a particular detector 210 corresponds to a particular scattering angle, independent of the location of volume element 156 of suspect object 172 within enclosure 168.

In accordance with an embodiment of the invention, both angular and energy distributions of the Bragg-scattered x-ray beam 250 are measured simultaneously. Thus, a given source of coherent-scattering provides a photon of energy multiplex advantage since count rates are increased, all angles of interest being recorded simultaneously. Thus, a given source of coherent-scatter provides a photon of energy $E_1$ into a detector at scatter angle $\theta_1$, and, simultaneously, a photon of energy $E_2$ into a detector at scatter angle $\theta_2$, both photons obeying Eqn. 2. Thus, crystal spacing d can be determined with increased signal-to-noise relative to systems wherein only the angular distribution is measured for a monochromatic beam, or only the energy spectrum is measured at a fixed angle. As apparent from Eqn. 2, the crystal spacing d is inversely proportional to the product of x-ray energy E and scattering angle $\theta$, and thus a given spacing is readily recognized as a hyperbola in the E-$\theta$ plane.

By integrating the screening and the verification operations, it becomes practical to make an economical scanning system that may provide high throughput, high detection efficiency and a very low false alarm rate. Increased speed of inspection may be obtained since scrutiny by a Bragg detector is reserved for only those objects within the enclosure which are suspected on the basis of side-scatter inspection.

In addition, counting all of the x-rays coherently-scattered from a volume element of a suspect object by employing a relatively large array of detectors of the coherently-scattered radiation permits a much more accurate assessment of the material constituting the volume element of the suspect object. Thorough counting allows full use of the Bragg equation which, for these higher x-ray energies, reduces to $\theta E$=constant. The energy spectrum is measured at each angle $\theta$. Since a specific material gives a spectrum for each detector, the spectrum corresponding to that specific material can be correlated with the spectrum for each detector element. The fully correlated spectrum is far more discriminating than the spectrum taken at just one angle.

A problem with energy-dispersive Bragg scattering is that beam hardening due to intervening absorption of x-ray radiation within enclosure 168 strongly reduces the low energy peaks relative to the higher energy peaks. Thus the signature of a target compound such as an explosive or drug may be distorted. To correct for that distortion, in accordance with the present invention, a fiducial material 232 is rotated in and out of x-ray beam path 269. Fiducial material 232 may be a reference crystal and is selected so that the scattering peaks of fiducial material 232 preferably lie outside the peaks that identify the sought for material. If the peaks are truly distinct, then the fiducial material may also be in the scatter path always. The fiducial peak intensities, without absorption, are independently measured and stored. The intensities measured with the enclosure 168 in place are then corrected according to the ratio of the measured to stored values. These ratios are used to determine the absorption versus x-ray energy curve that is used to correct the intensity of the energy peaks caused by the material in the volume element of the suspect object. X-rays that are Bragg scattered from reference object 232 are detected in 257. Reference object 232 produces a spectrum in detector 257 that has been distorted by the absorption of x-ray beam 269 as it passes through enclosure 168. Comparing the observed spectrum with the spectrum produced without any intervening absorbing material gives a first order correction for the absorption of all of the Bragg scattered beams since all of the Bragg scatterings are through small angles and the total absorption correction for the scattered beams 246 and 248 will be close to that of primary beam 269. It should be noted however, that the extension to placing reference crystals in each path is straightforward but does involve additional detectors for measuring the Bragg scattering from the reference block.

Successive steps of the side-scatter screening and secondary-scattering inspection are shown in FIG. 3. FIG. 3a shows conveyor belt 170 carrying enclosure 168, concealing first object 172, in direction 380 through the plane of scanning x-ray beam 164 and transistor detector 132 and over side-scattering detectors (not shown). In FIG. 3b, the conveyor belt 170 halts in front of the Bragg array 276 for alignment of the x-ray source 260, collimator 262, and volume element 156, shown to be identified as suspect by techniques described above using side-scattering. The field of view of the Bragg detectors and collimators comprising the Bragg array 276 is moved to coincide with the location of the volume element of suspect object 156. The inspection process continues in FIG. 3c and FIG. 3d for enclosure 168 when side-scatter screening reveals a second object 373 and volume element of suspect object 358. Since the second volume element of suspect object 358 lies further from the x-ray source 260 than did the first volume element of suspect object 156, the Bragg array 276 lies further from the x-ray source 260 in order to maintain its field of view on the second volume element of suspect object 358.

In one embodiment of the invention, x-rays having energies up to 160 keV are used in both side-scattering and coherent-scattering. For purposes of estimating throughput, assume that the conveyor belt travels at about 15 cm/second and halts in about 0.1 second. During side-scattering, a rotating wheel, with 6 hollow spokes and with the anode of a 160 keV, 3 kW x-ray source fit into its center, scans pencil x-ray beams about 3 mm in diameter across the enclosure. Side-scattering locates an object to a resolution of less than about 2 cm. An array approximately 10 cm in diameter containing approximately 100 detectors measuring Bragg intensity for about 0.1 seconds completes a Bragg scattering measurement in about 0.5 seconds. If an enclosure contains 8 suspicious volumes, the time required to inspect with Bragg scattering is about 10 seconds.

Other benefits accruing to this embodiment include more convenient conveyor belt operation and multitasking of equipment. The conveyor belt 170 need not be reversed following scanning the enclosure 168 for side-scattering. Indeed, Bragg measurements may advantageously be made while enclosure 168 is in motion on conveyor belt 170. For example, if the belt is moving at a speed of 1 inch per second, and if a Bragg measurement may be made in 0.1 seconds, then Bragg inspection with a spatial resolution on the order of 0.1 inches may be made while the belt is in motion.

The same x-ray source 160 can also be used both for detection of side-scattering and for detection of coherent-scattering. After the enclosure 168 has been scanned for side-scattering, the x-ray source 160 can be transported from the hub 163 of mechanical rotating wheel 161 to a position aligned with the input to pencil-beam collimator 262.

Figure 4A:
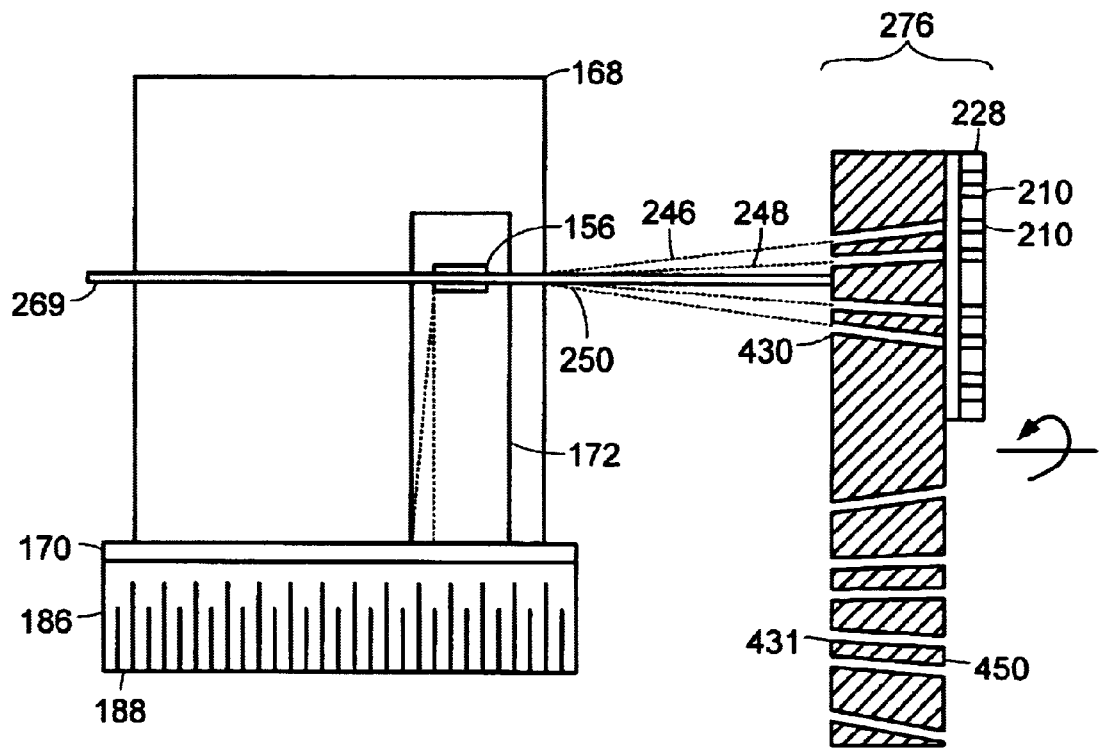
FIGS. 4a–4c are schematic elevation views of a method for x-ray inspection in accordance with further embodiments of the present invention using coherent-scattering.
Figure 4B:
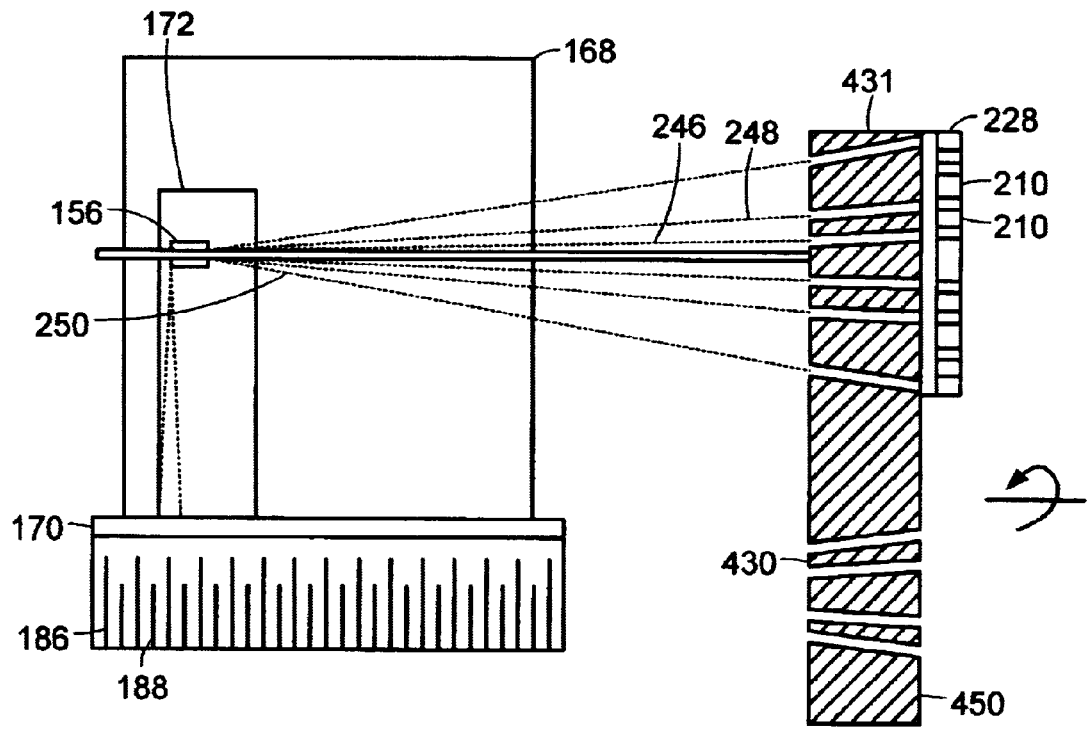
Figure 4C:
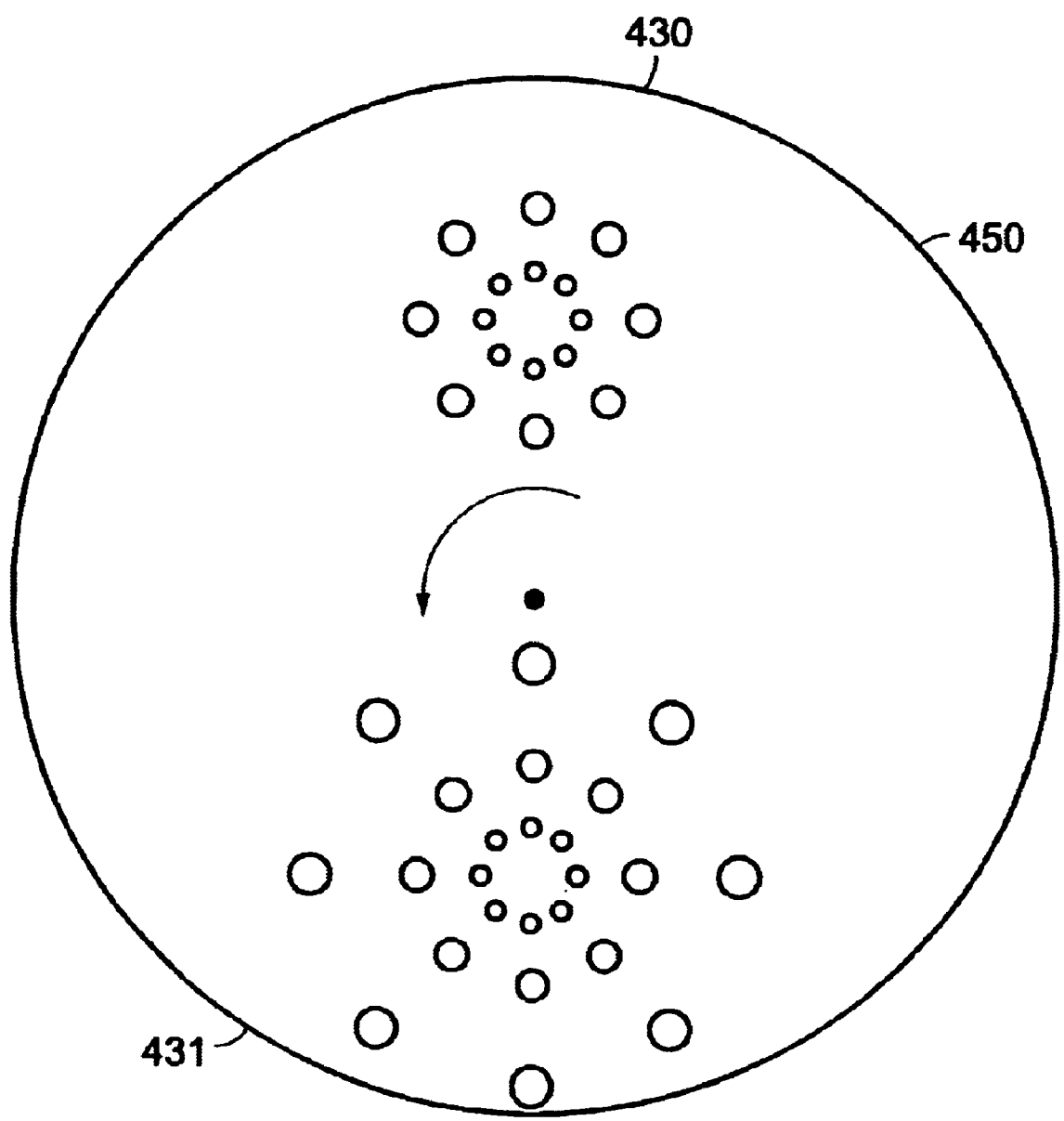

FIG. 4 illustrates another embodiment where Bragg scatter detector array 228 is held fixed relative to conveyor 170 and enclosure 168 and collimator disk 450 containing collimator array 430 and collimator array 431 is mounted between detector array 228 and irradiated volume element of suspect object 156. The field of view of collimator array 430 (FIG. 4a) lies closer to detector array 228 than does the field of view of collimator 431 (FIG. 4b). When side-scatter detector arrays 186 reveal the position of irradiated volume element 156 to be closer to detector array 228, collimator array 430 is rotated between volume element 156 and detector array 228. When side-scatter detector arrays 186 reveal the position of irradiated volume element 156 to be further away from detector array 228, collimator array 431 is rotated between volume element 156 and detector array 228. As a result, irradiated volume element 156 is maintained in the field of view of the detectors without movement of detector array 228. FIG. 4c contains a front view of collimator disk 450 showing collimator arrays 430 and 431.

The described embodiments of the invention are intended to be merely exemplary and numerous variations and modifications will be apparent to those skilled in the art. All such variations and modifications are intended to be within the scope of the present invention as defined in the appended claims.

What is claimed is:

1. A method for inspecting an enclosure, the method comprising:
    a. irradiating the enclosure with penetrating radiation emanating from a source;
    b. detecting radiation side-scattered from an object within the enclosure;
    c. locating the position of the object from the side-scattered radiation;
    d. determining whether the object is a suspect object on the basis of the side-scattered radiation;
    e. irradiating a volume element of the suspect object with penetrating radiation;
    f. detecting radiation coherently-scattered by the volume element of the suspect object in such a manner that the correspondence between a particular detector element and a given scattering angle is substantially independent of the location of the volume element of the suspect object within the enclosure;
    g. determining at least one of an energy spectrum and an angular distribution of radiation coherently-scattered by the volume element of the suspect object; and
    h. characterizing the volume element of the suspect object on the basis of at least one of the energy spectrum and the angular distribution of the coherently-scattered radiation.

2. The method according to claim 1, wherein the step of determining whether the object is a suspect object includes the step of calculating a characteristic mass density of the object based on at least the side-scattered radiation.

3. The method according to claim 1, wherein the step of determining whether the object is a suspect object on the basis of side-scattered radiation includes the step of identifying the object on the basis of mass densities of contiguous volume elements of the object.

4. The method according to claim 1, wherein the step of detecting radiation side-scattered from an object includes detecting x-rays Compton scattered from the object.

5. The method according to claim 1, wherein the step of irradiating the enclosure further includes the step of generating a scanning x-ray beam.

6. The method according to claim 5, wherein the step of generating a scanning x-ray beam includes the step of mounting a first x-ray source at the center of a rotating wheel having a plurality of hollow spokes.

7. The method according to claim 1, wherein the step of irradiating the enclosure further includes the step of generating x-rays of energy less than 160 keV.

8. The method according to claim 1, wherein the step of irradiating the volume element of the suspect object with penetrating radiation further includes the steps of aligning a single pencil-beam collimator with a second x-ray source and with the volume element of the suspect object.

9. The method according to claim 1, wherein the step of irradiating the volume element of the suspect object with penetrating radiation further includes the step of generating x-rays of energy less than 160 keV.

10. The method according to claim 1, wherein the step of detecting radiation coherently-scattered from the volume element of the suspect object further includes the step of causing the field of view of a Bragg scatter detector array to coincide with the volume element of the suspect object.

11. The method according to claim 1, further including the step of transporting the enclosure on a conveyor belt in a specified conveyor direction.

12. The method according to claim 11, wherein the steps of irradiating the enclosure with penetrating radiation and detecting radiation side-scattered from the object occur as the conveyor belt moves.

13. The method according to claim 11, wherein the steps of irradiating the enclosure with penetrating radiation and detecting radiation coherently-scattered from the object occur as the conveyor belt moves.

14. The method according to claim 11, further comprising the step of halting the conveyor belt prior to irradiating the volume element of the suspect object.

15. The method according to claim 14, further including the step of determining whether another object is a suspect object.

16. The method according to claim 1, wherein the step of irradiating the volume element of the suspect object is performed with the source of step (a).

17. The method according to claim 11, wherein the step of irradiating the volume element of the suspect object is performed with the source of step (a).

18. The method of claim 17, further including the step of advancing the source of step (a) in the conveyor direction.

19. An inspection system for characterizing an object contained within an enclosure, the system comprising:

a. a first and a second source for producing a first and a second beam of penetrating radiation;

b. a scanner for scanning the first beam through successive positions with respect to the enclosure;

c. a conveyor for transporting the enclosure through the scanned first beam;

d. a set of detectors disposed along a direction substantially parallel to the first beam, the set of detectors generating a side-scatter signal based on penetrating radiation from the first beam side-scattered by the object;

e. a controller for identifying a position of a suspect object based at least in part upon the side-scatter signal; and f. a plurality of Bragg detectors with fields of view coinciding with a single volume element and disposed along a direction substantially transverse to the second beam for measuring at least one of an energy spectrum and an angular distribution of coherently-scattered penetrating radiation.

20. The inspection system of claim 19, wherein the Bragg detectors move together as an array in a direction substantially along the second beam such that their fields of view coincide with a single volume element coincident with the second beam.

21. The inspection system of claim 19, wherein the same source produces the first and the second beams of penetrating radiation.

22. The inspection system of claim 19, wherein the controller causes the conveyor to halt with the second beam irradiating the suspect object.

23. The inspection system of claim 19, wherein the scanner comprises a rotating wheel made of material opaque to the radiation with a plurality of hollow spokes and a hollow center.

24. A method for inspecting an enclosure, the method comprising:

a. irradiating the enclosure with a beam of penetrating radiation emanating from a source;

b. detecting radiation side-scattered from an object within the enclosure;

c. locating the position of the object based on the side-scattered radiation;

d. determining whether the object is a suspect object on the basis of the side-scattered radiation;

e. irradiating a volume element of the suspect object with penetrating radiation;

f. detecting radiation coherently-scattered by the volume element of the suspect object into a plurality of detector elements in such a manner that the correspondence between a particular detector element of the plurality of detector elements and a given scattering angle holds uniquely for the irradiated volume element of the suspect object;

g. determining at least one of an energy spectrum and an angular distribution of radiation coherently-scattered by the volume element of the suspect object; and h. characterizing a material composition of the volume element of the suspect object on the basis of at least one of the energy spectrum and the angular distribution of the coherently-scattered radiation.

25. The method in accordance with claim 24, wherein the step of detecting radiation coherently-scattered from the volume element of the suspect object further includes the step of matching a field of view of a scatter detector array to the volume element of the suspect object.

26. The method in accordance with claim 25, wherein the step of matching a field of view of the scatter detector array to the volume element of the suspect object further includes:

a. rotating a structure containing a plurality of collimating structures, each structure corresponding to a specified distance along the beam from the volume element to the scatter detector array; and b. measuring the output of the scatter detector array at least when the volume element of the suspect object and the array are separated by the specified distance.

27. The method in accordance with claim 26, further including the step of halting rotation of the structure during measurement of the output of the scatter detector.

* * * * *